United States Patent [19]

Lin et al.

[11] 4,371,724

[45] Feb. 1, 1983

[54] ETHANOL SYNTHESIS BY HOMOLOGATION OF METHANOL

[75] Inventors: Jiang-Jen Lin; John F. Knifton, both of Austin, Tex.

[73] Assignee: Texaco Inc., White Plains, N.Y.

[21] Appl. No.: 224,199

[22] Filed: Jan. 8, 1981

[51] Int. Cl.³ .............................................. C07C 27/00
[52] U.S. Cl. .................................................... 568/902
[58] Field of Search ........................................ 568/902

[56] References Cited

U.S. PATENT DOCUMENTS 3,285,948 11/1966 Butler .................................. 568/902
4,239,924 12/1980 Pretzer et al. ..................... 568/902
4,277,634 7/1981 Walker ............................... 568/902

*Primary Examiner*—Alan Siegel
*Attorney, Agent, or Firm*—Jack H. Park; Walter D. Hunter

[57] ABSTRACT

Ethanol is prepared by contacting methanol, hydrogen and carbon monoxide with a catalyst system comprising a ruthenium compound, a quaternary phosphonium or ammonium base or salt and a cobalt compound such as cobalt iodide in the presence of a non-polar, substantially inert, oxygenated hydrocarbon solvent.

23 Claims, No Drawings

ETHANOL SYNTHESIS BY HOMOLOGATION OF METHANOL

BACKGROUND OF THE INVENTION

1. Field of the Invention

This invention relates to an improved process for preparing ethanol from methanol by reaction with hydrogen and carbon monoxide.

2. Prior Art

A great number of processes have been described in the art for reacting methanol with carbon monoxide and hydrogen in the presence of catalyst systems to produce ethanol. A general disadvantage of the art described processes is that they all produce a wide variety of other related products such as higher molecular weight alcohols, aldehydes, ketones, carboxylic acids, esters, etc. in addition to the desired ethanol.

In U.S. Pat. No. 3,285,948, for example, a method of forming alcohols is set out in which a cobalt catalyst system comprising cobalt carbonyl, an iodine promoter and a ruthenium halide is described. Cawse discloses in U.S. Pat. No. 4,013,700 a process for preparing polyhydric alcohols, etc. by reacting hydrogen and carbon monoxide in the presence of a quaternary phosphonium salt and a rhodium carbonyl at elevated temperature and pressure. Riley et al. teach in U.S. Pat. No. 3,248,432 the preparation of ethanol by the reaction of methanol, carbon monoxide, and hydrogen in the presence of a cobalt compound and an iodine promoter. Likewise in British Pat. No. 1,546,428 the preparation of ethanol by reacting methanol with carbon monoxide and hydrogen in the presence of a solvent such as hydrocarbon solvent, a cobalt-containing catalyst such as cobalt iodide or bromide and a tertiary phosphine. Slinkard in U.S. Pat. No. 4,168,391 teaches a process for preparing ethanol by reaction of carbon monoxide, hydrogen and methanol in the presence of cobalt carbonyl and an oxygenated solvent such as dioxane.

All of the processes described above suffer from one or more disadvantages. In most cases the conversion of methanol is low and a wide variety of products in addition to the desired ethanol are formed with consequent separation and disposal problems.

SUMMARY OF THE INVENTION

In the process of this invention ethanol is prepared in high yield by reacting methanol with a mixture of hydrogen and carbon monoxide. More particularly, this invention relates to a process for preparing ethanol by contacting methanol, hydrogen and carbon monoxide with a catalyst system comprising a ruthenium compound, a quaternary phosphonium or ammonium base or salt and a cobalt compound such as cobalt iodide in the presence of an oxygenated hydrocarbon solvent at an elevated temperature and pressure.

Recovery of ethanol from the reaction product can be carried out in any conventional or convenient manner such as by distillation, extraction, etc.

DETAILED DESCRIPTION OF THE INVENTION

The catalyst systems suitable for the practice of this invention comprise a ruthenium compound, a quaternary phosphonium base or salt and a cobalt compound as exemplified by cobalt iodide. These catalyst systems give substantially higher yields of ethanol than can be obtained when the catalyst utilized is solely a ruthenium compound together with the quaternary base or salt. Likewise, when the catalyst system employed comprises, for example, only cobalt iodide and a tetraalkyl phosphonium salt, such as tetrabutylphosphonium bromide, no ethanol is formed. Furthermore, a high degree of conversion of methanol to the desired ethanol is achieved in this process. Also, the stability of this catalyst system is such that it can be conveniently recovered from the reaction mixture and recycled to the process.

Generally, with regard to the metallic components of the catalyst system it will contain from about 20 to about 80 mole percent of the ruthenium compound with the balance being cobalt iodide, based on the total number of moles of the ruthenium compound and the total number of moles of the cobalt compound in the system. Preferably, the catalyst system will contain about equimolar amounts of the ruthenium and cobalt compounds.

A wide variety of ruthenium compounds may be utilized in the catalyst system of this invention. For instance, the ruthenium may be added to the reaction mixture in an oxide form, as in the case of, for example, ruthenium(IV) oxide, hydrate, anhydrous ruthenium-(IV) dioxide and ruthenium(VIII) tetraoxide. Alternatively, it may be added as the salt of a mineral acid, as in the case of ruthenium(III) chloride hydrate, ruthenium-(II) bromide, anhydrous ruthenium(III) chloride and ruthenium nitrate, or as the salt of a suitable organic carboxylic acid, for example, ruthenium(III) acetate, ruthenium(III) propionate, ruthenium butyrate, ruthenium(III) trifluoroacetate, ruthenium octanoate, ruthenium naphthenate, ruthenium valerate and ruthenium-(III) acetylacetonate. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Cobalt compounds suitable for use in this ruthenium-cobalt bimetallic catalyst system are the cobalt(II) iodide, cobalt(II) bromide and cobalt(II) chloride. If desired, the cobalt(II) iodide can be generated in situ by adding the combination of cobalt and elemental iodide or hydrogen iodine to the reactor.

Quaternary phosphonium salts suitable for use in this process have the formula:

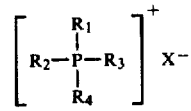

where $R_1$, $R_2$, $R_3$ and $R_4$ are organic radicals, particularly alkyl, aryl or alkaryl radicals bonded to the phosphorous atom, and X is an anionic species. The organic radicals useful in this instance include those alkyl radicals having 1 to 20 carbon atoms in a branched or linear alkyl chain; they include, for example, the methyl, ethyl, n-butyl, iso-butyl, octyl, 2-ethylhexyl and dodecyl radicals. Tetraoctylphosphonium bromide and tetrabutylphosphonium bromide are typical examples presently in commercial production. The corresponding quaternary phosphonium and ammonium acetates, hydroxides, nitrates, chromates, tetrafluoroborates and other halides, such as the corresponding chlorides, and iodides, are also satisfactory in this instance. Also useful are the corresponding quaternary ammonium bases and salts of the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus or nitrogen atom through the aryl function.

Illustrative examples of suitable quaternary phosphonium and ammonium bases and salts include tetrabutylphosphonium bromide, tetraoctylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide.

The preferred quaternary salts are generally the tetralkylphosphonium or alkyl-triaryl salts containing alkyl groups having 3–8 carbon atoms, such as butyl, hexyl and octyl and where the aryl group is phenyl. Tetrabutylphosphonium salts, such as tetrabutylphosphonium bromide, constitute a preferred group of tetraalkylphosphonium salts for the practice of this invention.

Preferred tetrabutylphosphonium salts or bases include the bromide, chloride, iodide, acetate, the chrome salts and hydroxide base. Preferred alkyl-triaryl phosphonium salts include, for example, heptyltriphenylphosphonium bromide, butyltriphenylphosphonium bromide, and methyltriphenylphosphonium bromide as well as the corresponding chlorides.

Generally, in the catalyst system the molar ratio of the ruthenium compound to the quaternary phosphonium or ammonium salt or base will range from about 1:0.01 to about 1:100 or more and, preferably, will be from about 1:0.5 to about 1:20.

The quantity of ruthenium compound employed in the instant invention is not critical and may vary over a wide range. In general, the novel process is desirably conducted in the presence of a catalytically effective quantity of the active ruthenium species and of the cobalt iodide which gives the desired product in reasonable yield. The reaction proceeds when employing as little as about $1 \times 10^{-6}$ weight percent, and even lesser amounts, of ruthenium together with about $1 \times 10^{-6}$ weight percent or less of cobalt, basis the total weight of the reaction mixture. The upper concentration is dictated by a variety of factors including catalyst cost, partial pressures of carbon monoxide and hydrogen, operating temperature etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention.

This solvent useful in the process of this invention is an oxygenated hydrocarbon i.e., a compound composed only of carbon, hydrogen and oxygen and one in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions, it must be relatively non-polar and it must be one which has a normal boiling point of at least 65° C. at atmospheric pressure and preferably, the solvent will have a boiling point greater than that of ethanol and other oxygen-containing reaction products so that recovery of the solvent by distillation is facilitated.

Preferred ester type solvents are the aliphatic and acrylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such as 1,4-dioxane, etc.

The temperature range which can usefully be employed in these syntheses is a variable dependent upon other experimental factors, including the pressure, and the concentration and choice of a particular species of ruthenium catalyst among other things. The range of operability is from about 150° to 350° C. when superatmospheric pressures of syngas are employed. A narrow range of 180°–250° C. represents the preferred temperature range.

Superatmospheric pressures of 500 psi or greater lead to substantial yields of ethanol by the process of this invention. A preferred operating range is from 2000 psi to 10,000 psi, although pressures above 10,000 psi also provide useful yields of ethanol.

The relative amounts of carbon monoxide and hydrogen which may be initially present in the syngas mixture can be varied widely. In general, the mole ratio of CO to $H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Higher alcohols and carboxylic acid esters may also be formed while carrying out the process of this invention. Most often these derivatives are n-propanol, methyl formate, methyl acetate, ethyl acetate, ethyl ether, etc. The major by-products of the process such as the higher molecular weight alcohols and carboxylic acid esters, are, of course, also useful compounds and major articles of commerce. The higher alcohols, the carboxylic acid esters and ethers can easily be separated from one another by conventional means, e.g., fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the ethanol product, and after recovery of the alcohol and other products, a fraction rich in ruthenium catalyst components may then be recycled to the reaction zone, if desired, and additional products generated.

The products have been identified in this work by one or more of the following analytical procedures, viz, gas-liquid phase chromatograph (GLC), infrared (IR), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples illustrate the novel process of this invention.

EXAMPLE 1

A glass reactor liner was charged with 0.57 g (3.0 mmoles) of hydrated ruthenium(IV) dioxide, 10.2 g (30 mmoles) of n-tetrabutylphosphonium bromide, 1.9 g (6.0 mmoles) of cobalt(II) iodide, 30 ml of methanol and 70 ml of p-dioxane. The glass liner was placed in a stainless steel reactor. The reactor was purged of air and pressured to 1000 psi with a mixture of carbon monoxide and hydrogen (1:2 molar) then was heated to 200° C., while it was agitated by rocking. The pressure was brought up to 3400 psi and constant pressure was maintained by repressuring from a surge tank.

The reaction was stopped after 10 hours and the reactor cooled to room temperature. An off-gas sample was taken and excess gas vented from the reactor following which 115.8 g of a reddish-brown product was recovered.

Analysis of the liquid product by GLC showed the following product composition:
74 mole % ethanol
4 mole % n-proponol
0 mole % methyl formate
1 mole % ethyl acetate
0 mole % ethyl ether The methanol conversion was calculated to be 80 mole percent. The water content as determined by Karl Fischer titration was 2.06 mole percent.

A typical off-gas sample showed the presence of:
33.8% hydrogen
8.2% carbon monoxide
40.0% carbon dioxide
0.5% ethane

EXAMPLE 2

In this comparative example the experimental procedure of Example 1 was followed. The reactor was charged with 0.31 g (1.0 mmole) of cobalt(II) iodide, 1.7 g (5.0 mmoles) of tetrabutylphosphonium bromide, 8 ml of methanol and 20 ml of p-dioxane. No ruthenium was present in this run. After pressuring to 1000 psi with a mixture of carbon monoxide and hydrogen (1:2 molar), the reactor was heated to 200° C.; while it was agitated by rocking. The pressure was brought up to 3900 psi and constant pressure was maintained by repressuring from a surge tank. After 18 hours, the reactor was cooled rapidly and the residual pressure (2330 psi) was noted. Excess gas was removed by depressuring and a reddish-brown liquid product (29.9 g) recovered from the glass reactor liner.

Analysis of the liquid product by GLC showed the presence of 47 mole percent of ethyl acetate and no ethanol was detected. The methanol conversion was 30 mole percent.

EXAMPLE 3

The reactor was charged with 0.10 g (0.5 mmole) of ruthenium(IV) dioxide hydrate, 1.70 g (5.0 mmoles) of n-tetrabutylphosphonium bromide, 8 ml of methanol and 20 ml of p-dioxane. No cobalt(II) iodide was present in this run. The reactor was pressured to 2000 psi with a mixture of carbon monoxide and hydrogen (1:2 molar) and then heated to a temperature of 200° C. while it was agitated by rocking. The pressure was brought up to 6400 psi and these conditions of temperature and pressure held for 18 hrs. No surge tank was used and the pressure dropped to 5400 psi during the reaction process.

At the end of 18 hours the reactor was cooled, an off-gas sample was taken and the excess gas released. The reddish-brown liquid product recovered (28.8 g) was analyzed by GLC to give 61 mole percent ethanol product selectivity. Methanol conversion was 11 percent.

This experiment showed the very low conversion of methanol to ethanol when the catalyst system does not contain cobalt iodide.

EXAMPLE 4

Following the general procedure of Examples 1-3 inclusive, a glass liner reactor was charged with 0.57 g (3.0 mmoles) of hydrated ruthenium oxide, 10.2 g (30 mmoles) tetra-n-butylphosphonium bromide, 1.9 g (6 mmoles) of cobalt(II) iodide, 30 ml of methanol and 70 ml of p-dioxane. After flushing with syngas (CO/H$_2$ mixture), the reactor was pressured to 1000 psi with a gaseous mixture containing 2 moles of hydrogen per mole of carbon monoxide, and heated to 200° C. with agitation. Then the pressure was brought up to 3400 psi and these conditions were maintained for 15 hours. After the indicated reaction time, the reactor was cooled and vented and the reddish-brown product recovered and analyzed by GLC and Karl Fischer Titration. There were no residual solids at this stage.

The product liquid was distilled at atmospheric pressure and a distillate fraction was collected at bp range of ca. 60°–100° C. The residual catalyst remained behind as a deep-brown colored liquid (ca. 9.5 g). An aliqnot of residual catalyst liquid (ca. 4.5 g), 8 ml of methanol and 24 ml of p-dioxane was charged to the glass liner reactor. The reactor was sealed, flushed with syngas, pressured to 1000 psi with CO/H$_2$ (1:2) and heated to 200° C. with agitation. The pressure was brought up to 5000 psi and maintained for 18 hours. In this manner the synthesis of ethanol was repeated successfully, and the latter recovered from the crude liquid product by simple distillation.

The residual catalyst solution (5.0 g) from this second cycle was again returned to the reactor for further ethanol synthesis. The syngas pressures of 4160 psi and 3750 psi were used for the third and fourth cycles respectively. The methanol conversion and ethanol selectivity for this four cycle experiment are shown in Table I, modify line numbering 0

TABLE I
SYNTHESIS OF ETHANOL FROM METHANOL AND SYNGAS-CATALYST RECYCLING

| EXAMPLE | NUMBER OF CATALYST CYCLES | METHANOL CONVERSION | ETHANOL SELECTIVITY |
|---------|---------------------------|---------------------|---------------------|
| 4       | 1                         | 80                  | 74                  |
|         | 2                         | 88                  | 73                  |
|         | 3                         | 86                  | 70                  |
|         | 4                         | 69                  | 77                  |

EXAMPLES 5-7

Using the procedures and ruthenium-cobalt catalyst of Example 1, methanol homologation to ethanol was conducted at 200° C., and 3400 psi operating pressure for various reaction periods. Table II summerizes the results for methanol conversion and ethanol selectivity.

TABLE II

| EXAMPLE | OPERATING PRESSURE (psi) | TIME (hr.) | Ru/Co Molar ratio | MeOH Conversion | EtOH Selectivity |
|---------|--------------------------|------------|-------------------|-----------------|------------------|
| 5       | 3400                     | 1          | 1:2               | 22              | 62               |
| 6       | 3400                     | 5          | 1:2               | 44              | 83               |
| 7       | 3400                     | 9          | 1:2               | 70              | 79               |

What is claimed is:

1. A process for preparing ethanol which comprises contacting a mixture of carbon monoxide, hydrogen and methanol with a catalyst system comprising a ruthenium compound, a quaternary phosphonium or ammonium base or salt and a cobalt compound selected from the group consisting of cobalt(II) iodide, cobalt(II) bromide and cobalt(II) chloride, in the presence of an inert liquid oxygenated hydrocarbon solvent and at a pressure of 500 psi or greater and at a temperature of at least 150° C.

2. The process of claim 1 wherein the process is conducted at a pressure of about 2000 psi to about 10,000 psi.

3. The process of claim 1 wherein the process is conducted at a temperature of about 180°-250° C.

4. The process of claim 1 wherein the said ruthenium compound is selected from the group consisting of anhydrous ruthenium(IV) dioxide, ruthenium(IV) dioxide hydrate, ruthenium(VIII) tetraoxide, ruthenium(III) trichloride, ruthenium acetate, ruthenium propionate, ruthenium(III) acetylacetonate and triruthenium dodecocarbonyl.

5. The process of claim 1 where the said ruthenium compound is ruthenium(IV) dioxide hydrate.

6. The process of claim 1 wherein the said ruthenium compound is ruthenium(III) trichloride.

7. The process of claim 1 wherein the said quaternary is a tetraalkylphosphonium salt.

8. The process of claim 1 wherein the said quaternary is an alkyl-triarylphosphonium salt.

9. The process of claim 1 wherein the said quaternary is a tetrabutylphosphonium salt.

10. The process of claim 1 wherein the said quaternary is an alkyl-triphenylphosphonium salt.

11. The process of claim 1 wherein the said quaternary is selected from the group consisting of tetrabutylphosphonium chloride, tetrabutylphosphonium bromide, tetrabutylphosphonium iodide, tetrabutylphosphonium acetate, tetrabutylphosphonium chromate and tetrabutylphosphonium hydroxide.

12. The process of claim 1 wherein the said quaternary is tetrabutylphosphonium bromide.

13. The process of claim 1 wherein the said quaternary is selected from the group consisting of heptyltriphenylphosphonium bromide, heptyltriphenylphosphonium chloride, and methyltriphenylphosphonium bromide.

14. The process of claim 1 wherein the said quaternary is heptyltriphenylphosphonium bromide.

15. The process of claim 1 wherein the said hydrocarbon solvent is selected from the group consisting of 1,3-dioxane, 1,4-dioxane, isopropyl propyl ether, diethylene glycol dibutyl ether, dibutyl ether and ethyl butyl ether.

16. The process of claim 1 wherein the said quaternary is a tetraalkylphosphonium bromide and the hydrocarbon solvent is selected from the group consisting of 1,3-dioxane, 1,4-dioxane, isopropyl propyl ether, diethylene glycol dibutyl ether, dibutyl ether and ethyl butyl ether.

17. The process of claim 1 wherein the said ruthenium compound is hydrated ruthenium(IV) dioxide, the said quaternary is tetrabutylphosphonium bromide and the said hydrocarbon solvent is 1,4-dioxane.

18. The process of claim 1 wherein the said quaternary is a quaternary phosphonium base.

19. The process of claim 18 wherein the said quaternary is tetrabutylphosphonium hydroxide.

20. The process of claim 1 wherein the said ruthenium compound is ruthenium oxide and the said quaternary is a quaternary phosphonium base.

21. The process of claim 1 wherein the said quaternary is a quaternary ammonium base.

22. The process of claim 21 wherein the said quaternary is tetramethylammonium hydroxide.

23. The process of claim 1 wherein the said ruthenium compound is ruthenium oxide and the said quaternary is a quaternary ammonium base.

* * * * *